(12) United States Patent
Bojarski et al.

(10) Patent No.: US 9,173,653 B2
(45) Date of Patent: *Nov. 3, 2015

(54) TISSUE REPAIR DEVICE

(71) Applicant: Smith & Nephew, Inc., Memphis, TN (US)

(72) Inventors: Raymond A. Bojarski, Attleboro, MA (US); George Sikora, Bridgewater, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/138,223

(22) Filed: Dec. 23, 2013

(65) Prior Publication Data

US 2014/0114353 A1    Apr. 24, 2014

Related U.S. Application Data

(60) Continuation of application No. 13/196,118, filed on Aug. 2, 2011, now Pat. No. 8,623,051, which is a division of application No. 11/165,551, filed on Jun. 24, 2005, now abandoned.

(51) Int. Cl.
*A61B 17/04*     (2006.01)
*A61B 17/00*     (2006.01)

(52) U.S. Cl.
CPC ......... *A61B 17/0401* (2013.01); *A61B 17/0487* (2013.01); *A61B 2017/00004* (2013.01); *A61B 2017/00526* (2013.01); *A61B 2017/044* (2013.01); *A61B 2017/0458* (2013.01);

(Continued)

(58) Field of Classification Search
CPC ............... A61B 2017/0475; A61B 2017/0477; A61B 2017/0462; A61B 17/0487; A61B 17/0401; A61B 2017/0464; A61B 2017/0458; A61B 2017/00526; A61B 2017/044; A61B 2017/00004; Y10T 24/3916
USPC ......................... 606/151, 228, 232; 24/129 R
See application file for complete search history.

(56) References Cited

U.S. PATENT DOCUMENTS

| 233,475 A | 10/1880 | Cook et al. |
| 261,501 A | 7/1882 | Vandermark |

(Continued)

FOREIGN PATENT DOCUMENTS

| AU | 2005200304 | 12/2006 |
| EP | 260970 | 3/1988 |

(Continued)

OTHER PUBLICATIONS

International Search Report and Written Opinion for International Appl. No. PCT/US2006/024752, mailed Nov. 7, 2006.

(Continued)

*Primary Examiner* — Jing Ou
(74) *Attorney, Agent, or Firm* — Burns & Levinson LLP; Joseph M. Maraia

(57) ABSTRACT

A tissue repair device includes a closed knotless loop of multifilament flexible material, and a fixation member having a structure that defines a cavity that receives at least a part of the closed loop. The tissue repair device may include a flexible member traversing the loop. The loop may include a portion in which ends of the multifilament flexible material are thermally fused together. The multifilament flexible material may be braided or twisted.

4 Claims, 7 Drawing Sheets

(52) U.S. Cl.
CPC . *A61B2017/0464* (2013.01); *A61B 2017/0475* (2013.01); *A61B 2017/0477* (2013.01); *Y10T 24/3916* (2015.01)

(56) References Cited

U.S. PATENT DOCUMENTS

| | | |
|---|---|---|
| 1,260,264 A | 3/1918 | Huszar |
| 1,635,066 A | 7/1927 | Wells |
| 2,269,963 A | 1/1942 | Charles |
| 2,479,464 A | 8/1949 | Bliss |
| 2,610,631 A | 9/1952 | Calicchio |
| 2,880,728 A | 4/1959 | Rights |
| 2,881,762 A | 4/1959 | Lowrie |
| 3,011,185 A | 12/1961 | John |
| 3,409,014 A | 11/1968 | Grant |
| 3,470,875 A | 10/1969 | Johnson |
| 3,618,447 A | 11/1971 | Goins |
| 3,664,345 A | 5/1972 | Dabbs et al. |
| 3,716,058 A | 2/1973 | Tanner |
| 3,752,516 A | 8/1973 | Mumma |
| 3,752,519 A | 8/1973 | Nordell et al. |
| 3,757,629 A | 9/1973 | Schneider |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,867,944 A | 2/1975 | Samuels |
| 3,871,379 A | 3/1975 | Clarke |
| 3,910,281 A | 10/1975 | Kletschka et al. |
| 3,946,740 A | 3/1976 | Bassett |
| 3,976,079 A | 8/1976 | Samuels et al. |
| 3,977,050 A | 8/1976 | Perez |
| 3,985,138 A | 10/1976 | Jarvik |
| 4,006,747 A | 2/1977 | Kronenthal et al. |
| 4,039,753 A | 8/1977 | Balogh et al. |
| 4,141,087 A | 2/1979 | Shalaby et al. |
| 4,144,876 A | 3/1979 | DeLeo |
| 4,160,453 A | 7/1979 | Miller |
| 4,185,514 A | 1/1980 | Edwards |
| 4,235,238 A | 11/1980 | Ogiu et al. |
| 4,316,469 A | 2/1982 | Kapitanov |
| 4,326,531 A | 4/1982 | Shimonaka |
| 4,493,323 A | 1/1985 | Albright et al. |
| 4,505,274 A | 3/1985 | Speelman |
| 4,531,522 A | 7/1985 | Bedi et al. |
| 4,534,350 A | 8/1985 | Golden et al. |
| 4,570,623 A | 2/1986 | Ellison et al. |
| 4,595,007 A | 6/1986 | Mericle |
| 4,596,249 A | 6/1986 | Freda et al. |
| 4,602,635 A | 7/1986 | Mullhollan et al. |
| 4,616,650 A | 10/1986 | Green et al. |
| 4,624,254 A | 11/1986 | McGarry et al. |
| 4,635,637 A | 1/1987 | Schreiber |
| 4,636,121 A | 1/1987 | Miller |
| 4,641,652 A | 2/1987 | Hutterer et al. |
| 4,662,068 A | 5/1987 | Polonsky |
| 4,705,040 A | 11/1987 | Mueller et al. |
| 4,719,917 A | 1/1988 | Barrows et al. |
| 4,723,540 A | 2/1988 | Gilmer |
| 4,741,330 A | 5/1988 | Hayhurst |
| 4,741,336 A | 5/1988 | Failla et al. |
| 4,750,492 A | 6/1988 | Jacobs |
| 4,760,848 A | 8/1988 | Hasson |
| 4,781,190 A | 11/1988 | Lee |
| 4,809,695 A | 3/1989 | Gwathmey et al. |
| 4,824,839 A | 4/1989 | Bondinell et al. |
| 4,826,794 A | 5/1989 | Coosemans et al. |
| 4,841,960 A | 6/1989 | Garner |
| 4,846,793 A | 7/1989 | Leonard et al. |
| 4,858,608 A | 8/1989 | McQuilkin |
| 4,873,976 A | 10/1989 | Schreiber |
| 4,884,572 A | 12/1989 | Bays et al. |
| 4,887,601 A | 12/1989 | Richards |
| 4,890,615 A | 1/1990 | Caspari et al. |
| 4,895,148 A | 1/1990 | Bays et al. |
| 4,899,743 A | 2/1990 | Nicholson et al. |
| 4,917,699 A | 4/1990 | Chervitz |
| 4,923,461 A | 5/1990 | Caspari et al. |
| 4,950,285 A | 8/1990 | Wilk |
| 4,961,741 A | 10/1990 | Hayhurst |
| 4,983,176 A | 1/1991 | Cushman et al. |
| 4,988,243 A | 1/1991 | Proffitt |
| 4,994,028 A | 2/1991 | Leonard et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,201 A | 10/1991 | Asnis |
| 5,078,731 A | 1/1992 | Hayhurst |
| 5,084,050 A | 1/1992 | Draenert |
| 5,084,058 A | 1/1992 | Li |
| 5,087,263 A | 2/1992 | Li |
| 5,100,415 A | 3/1992 | Hayhurst |
| 5,102,421 A | 4/1992 | Anspach |
| 5,123,913 A | 6/1992 | Wilk et al. |
| 5,141,520 A | 8/1992 | Goble et al. |
| 5,149,329 A | 9/1992 | Richardson |
| 5,154,189 A | 10/1992 | Oberlander |
| 5,178,629 A | 1/1993 | Kammerer |
| 5,203,787 A | 4/1993 | Noblitt et al. |
| 5,207,753 A | 5/1993 | Badrinath |
| 5,211,650 A | 5/1993 | Noda |
| 5,217,470 A | 6/1993 | Weston |
| 5,219,359 A | 6/1993 | McQuilkin et al. |
| 5,224,946 A | 7/1993 | Hayhurst et al. |
| 5,234,426 A | 8/1993 | Rank et al. |
| 5,236,445 A | 8/1993 | Hayhurst et al. |
| 5,246,441 A | 9/1993 | Ross et al. |
| 5,258,015 A | 11/1993 | Li et al. |
| 5,258,016 A | 11/1993 | DiPoto et al. |
| 5,261,914 A | 11/1993 | Warren |
| 5,268,001 A | 12/1993 | Nicholson et al. |
| 5,269,809 A | 12/1993 | Hayhurst et al. |
| 5,279,539 A | 1/1994 | Bohan et al. |
| 5,282,809 A | 2/1994 | Kammerer et al. |
| 5,318,577 A | 6/1994 | Li |
| 5,320,633 A | 6/1994 | Allen et al. |
| 5,336,229 A | 8/1994 | Noda |
| 5,336,231 A | 8/1994 | Adair |
| 5,342,369 A | 8/1994 | Harryman |
| 5,354,299 A | 10/1994 | Coleman |
| 5,364,408 A | 11/1994 | Gordon |
| 5,405,354 A | 4/1995 | Sarrett |
| 5,417,691 A | 5/1995 | Hayhurst |
| 5,417,692 A | 5/1995 | Goble et al. |
| 5,437,680 A | 8/1995 | Yoon |
| 5,439,467 A | 8/1995 | Benderev et al. |
| 5,439,684 A | 8/1995 | Prewett et al. |
| 5,441,502 A | 8/1995 | Bartlett |
| 5,447,512 A | 9/1995 | Wilson et al. |
| 5,458,081 A | 10/1995 | Reichert |
| 5,458,608 A | 10/1995 | Wortrich |
| 5,467,786 A | 11/1995 | Allen et al. |
| 5,474,572 A | 12/1995 | Hayhurst |
| 5,490,750 A | 2/1996 | Gundy |
| 5,496,331 A | 3/1996 | Xu et al. |
| 5,500,000 A | 3/1996 | Feagin et al. |
| 5,501,692 A | 3/1996 | Riza |
| 5,520,696 A | 5/1996 | Wenstrom |
| 5,520,700 A | 5/1996 | Beyar et al. |
| 5,520,921 A | 5/1996 | Chalifoux |
| 5,522,820 A | 6/1996 | Caspari et al. |
| 5,522,844 A | 6/1996 | Johnson |
| 5,527,342 A | 6/1996 | Pietrzak et al. |
| 5,545,178 A | 8/1996 | Kensey et al. |
| 5,554,171 A | 9/1996 | Gatturna et al. |
| 5,562,684 A | 10/1996 | Kammerer |
| 5,573,286 A | 11/1996 | Rogozinski |
| 5,593,424 A | 1/1997 | Northrup |
| 5,601,557 A | 2/1997 | Hayhurst |
| 5,607,432 A | 3/1997 | Fucci |
| 5,609,597 A | 3/1997 | Lehrer |
| 5,641,256 A | 6/1997 | Gundy |
| 5,643,319 A | 7/1997 | Green et al. |

(56) References Cited

U.S. PATENT DOCUMENTS

| | | |
|---|---|---|
| 5,643,321 A | 7/1997 | McDevitt |
| 5,647,874 A | 7/1997 | Hayhurst |
| 5,658,299 A | 8/1997 | Hart |
| 5,665,112 A | 9/1997 | Thal |
| 5,690,676 A | 11/1997 | DiPoto et al. |
| 5,702,422 A | 12/1997 | Stone |
| 5,702,462 A | 12/1997 | Oberlander |
| 5,713,904 A | 2/1998 | Errico et al. |
| 5,720,753 A | 2/1998 | Sander et al. |
| 5,720,765 A | 2/1998 | Thal |
| 5,725,529 A | 3/1998 | Nicholson et al. |
| 5,725,581 A | 3/1998 | Branemark |
| 5,728,109 A | 3/1998 | Schulze et al. |
| 5,728,136 A | 3/1998 | Thal |
| 5,730,744 A | 3/1998 | Justin et al. |
| 5,746,754 A | 5/1998 | Chan |
| 5,749,898 A | 5/1998 | Schulze et al. |
| 5,782,862 A | 7/1998 | Bonutti |
| 5,782,864 A | 7/1998 | Lizardi |
| 5,796,127 A | 8/1998 | Hayafuji et al. |
| 5,797,928 A | 8/1998 | Kogasaka |
| 5,810,848 A | 9/1998 | Hayhurst |
| 5,814,069 A | 9/1998 | Schulze et al. |
| RE36,020 E | 12/1998 | Moore et al. |
| 5,843,087 A | 12/1998 | Jensen et al. |
| 5,846,254 A | 12/1998 | Schulze et al. |
| 5,860,983 A | 1/1999 | Wenstrom |
| 5,871,490 A | 2/1999 | Schulze et al. |
| 5,891,168 A | 4/1999 | Thal |
| 5,893,592 A | 4/1999 | Schulze et al. |
| 5,893,856 A | 4/1999 | Jacob et al. |
| 5,893,880 A | 4/1999 | Egan et al. |
| 5,895,395 A | 4/1999 | Yeung |
| 5,897,564 A | 4/1999 | Schulze et al. |
| 5,902,321 A | 5/1999 | Caspari et al. |
| 5,921,986 A | 7/1999 | Bonutti |
| 5,928,244 A | 7/1999 | Tovey et al. |
| 5,941,439 A | 8/1999 | Kammerer et al. |
| 5,948,002 A | 9/1999 | Bonutti |
| 5,954,747 A | 9/1999 | Clark |
| 5,964,765 A | 10/1999 | Fenton et al. |
| 5,964,783 A | 10/1999 | Grafton et al. |
| 5,976,127 A | 11/1999 | Lax |
| 5,980,524 A | 11/1999 | Justin et al. |
| 5,989,252 A | 11/1999 | Fumex |
| 5,993,458 A | 11/1999 | Vaitekunas et al. |
| 6,024,758 A | 2/2000 | Thal |
| 6,027,523 A | 2/2000 | Schmieding |
| 6,039,753 A | 3/2000 | Meislin |
| 6,045,574 A | 4/2000 | Thal |
| 6,056,320 A | 5/2000 | Khalifa et al. |
| 6,063,106 A | 5/2000 | Gibson |
| 6,066,146 A | 5/2000 | Carroll et al. |
| 6,074,395 A | 6/2000 | Trott et al. |
| 6,096,038 A | 8/2000 | Michelson |
| 6,096,060 A | 8/2000 | Fitts et al. |
| 6,117,160 A | 9/2000 | Bonutti |
| 6,143,017 A | 11/2000 | Thal |
| 6,143,387 A | 11/2000 | Kubler et al. |
| 6,152,934 A | 11/2000 | Harper et al. |
| 6,152,936 A | 11/2000 | Christy et al. |
| 6,156,039 A | 12/2000 | Thal |
| 6,165,203 A | 12/2000 | Krebs |
| 6,174,324 B1 | 1/2001 | Egan et al. |
| 6,193,754 B1 | 2/2001 | Seedhom |
| 6,217,591 B1 | 4/2001 | Egan et al. |
| 6,283,996 B1 | 9/2001 | Chervitz et al. |
| 6,286,746 B1 | 9/2001 | Egan et al. |
| 6,306,158 B1 | 10/2001 | Bartlett |
| 6,306,159 B1 | 10/2001 | Schwartz et al. |
| 6,319,263 B1 | 11/2001 | Levinson |
| 6,319,271 B1 | 11/2001 | Schwartz et al. |
| 6,358,271 B1 | 3/2002 | Egan et al. |
| 6,409,743 B1 | 6/2002 | Fenton |
| 6,432,123 B2 | 8/2002 | Schwartz et al. |
| 6,491,707 B2 | 12/2002 | Makower et al. |
| 6,500,184 B1 | 12/2002 | Chan et al. |
| 6,520,980 B1 | 2/2003 | Foerster |
| 6,524,317 B1 | 2/2003 | Ritchart et al. |
| 6,527,795 B1 | 3/2003 | Lizardi |
| 6,533,802 B2 | 3/2003 | Bojarski et al. |
| 6,554,852 B1 | 4/2003 | Oberlander |
| 6,585,730 B1 | 7/2003 | Foerster |
| 6,635,073 B2 | 10/2003 | Bonutti |
| 6,641,596 B1 | 11/2003 | Lizardi |
| 6,652,563 B2 | 11/2003 | Dreyfuss |
| 6,656,182 B1 | 12/2003 | Hayhurst |
| 6,669,705 B2 | 12/2003 | Westhaver et al. |
| 6,692,499 B2 | 2/2004 | Tormala et al. |
| 6,692,516 B2 | 2/2004 | West et al. |
| 6,770,076 B2 | 8/2004 | Foerster |
| 6,855,157 B2 | 2/2005 | Foerster et al. |
| 6,923,824 B2 | 8/2005 | Morgan et al. |
| 6,972,019 B2 | 12/2005 | Michelson |
| 6,972,027 B2 | 12/2005 | Fallin et al. |
| 7,153,312 B1 | 12/2006 | Torrie et al. |
| 7,163,563 B2 | 1/2007 | Schwartz et al. |
| 7,500,983 B1 | 3/2009 | Kaiser et al. |
| 2001/0010005 A1 | 7/2001 | Kammerer et al. |
| 2002/0019649 A1* | 2/2002 | Sikora et al. .................. 606/232 |
| 2002/0052629 A1* | 5/2002 | Morgan et al. ................ 606/232 |
| 2002/0091959 A1 | 7/2002 | Klein et al. |
| 2002/0095181 A1 | 7/2002 | Beyar |
| 2002/0133159 A1 | 9/2002 | Jackson |
| 2002/0147463 A1 | 10/2002 | Martinek |
| 2002/0156500 A1 | 10/2002 | Storz et al. |
| 2002/0165548 A1 | 11/2002 | Jutley |
| 2002/0173821 A1 | 11/2002 | Fenton et al. |
| 2003/0070004 A1 | 4/2003 | Mukundan et al. |
| 2003/0109900 A1 | 6/2003 | Martinek |
| 2003/0120277 A1 | 6/2003 | Berger |
| 2003/0130694 A1 | 7/2003 | Bojarski et al. |
| 2003/0236555 A1 | 12/2003 | Thornes |
| 2004/0002734 A1 | 1/2004 | Fallin et al. |
| 2004/0037094 A1 | 2/2004 | Muegge et al. |
| 2004/0092937 A1 | 5/2004 | Criscuolo et al. |
| 2004/0133238 A1 | 7/2004 | Cerier |
| 2004/0133239 A1 | 7/2004 | Singhatat |
| 2004/0138683 A1 | 7/2004 | Shelton et al. |
| 2004/0243131 A1 | 12/2004 | Dirks et al. |
| 2004/0267317 A1 | 12/2004 | Higgins et al. |
| 2005/0033363 A1 | 2/2005 | Bojarski et al. |
| 2005/0037150 A1 | 2/2005 | Lijima et al. |
| 2005/0143761 A1 | 6/2005 | Modesitt et al. |
| 2005/0187577 A1* | 8/2005 | Selvitelli et al. ............... 606/232 |
| 2005/0277961 A1 | 12/2005 | Stone et al. |
| 2005/0277986 A1 | 12/2005 | Foerster et al. |
| 2006/0190042 A1 | 8/2006 | Stone et al. |
| 2007/0083236 A1 | 4/2007 | Sikora et al. |
| 2008/0065114 A1 | 3/2008 | Stone et al. |
| 2008/0082128 A1 | 4/2008 | Stone |

FOREIGN PATENT DOCUMENTS

| | | |
|---|---|---|
| EP | 108912 | 11/1988 |
| EP | 315371 | 5/1989 |
| EP | 598219 | 5/1994 |
| EP | 632999 | 1/1995 |
| EP | 847727 | 6/1998 |
| EP | 913123 | 5/1999 |
| EP | 1013229 | 6/2000 |
| EP | 1444959 | 8/2004 |
| EP | 1568326 | 8/2005 |
| FR | 2422386 | 11/1979 |
| FR | 2731610 | 6/1997 |
| JP | 54166092 | 11/1979 |
| JP | 54166093 | 11/1979 |
| JP | 54176284 | 12/1979 |
| JP | 54178988 | 12/1979 |
| JP | 950770 | 8/1997 |
| WO | 9851241 | 11/1998 |
| WO | 9912480 | 3/1999 |
| WO | 0040159 | 7/2000 |
| WO | 02036020 | 5/2002 |

(56) References Cited

FOREIGN PATENT DOCUMENTS

| WO | 02091959 | 11/2002 |
|---|---|---|
| WO | 03001893 | 7/2003 |
| WO | 2004037094 | 11/2004 |
| WO | 2005037150 | 4/2005 |

OTHER PUBLICATIONS

Office Action for U.S. Appl. No. 10/278,474, mailed Jun. 9, 2009.
Office Action for U.S. Appl. No. 10/358,252, mailed May 28, 2009.
Office Action for U.S. Appl. No. 11/353,868, mailed May 22, 2009.
International Preliminary Report on Patentability for International Appl. No. PCT/US2006/076348, mailed Jun. 20, 2008.
Office Action for U.S. Appl. No. 10/918,445, mailed Mar. 31, 2009.
Annex to Form PCT/ISA/206 Communication Relating to the Results of the Partial International Search for International Appl. No. PCT/US2004/003258, mailed Jul. 30, 2004, 6 pages.
Office Action for European Appl. No. 01981796.4, mailed Apr. 21, 2005.
Sotereanos, D.G., "Rotator Cuff Repair using Panalok RC Absorbable Anchor", Jan. 1998.
Thal R., "A Knotless Suture Anchor & Method for Arthroscopic Bankart Repair Introduction", Poster Board.: 296 at the 1999 Annual Meeting of the American Academy of Orthopedic Surgeons.
Thal, R., "A Knotless Suture Anchor: Technique for Use in Arthroscopic Bankart Repair", Feb. 2001.
Unicom Surgical Sutures & Suture Needles, "Suture Needles Information", 2005.
U.S. Appl. No. 60/114,170, filed Dec. 30, 1988, Schwart et al.
Office Action for U.S. Appl. No. 10/278,474, mailed Aug. 14, 2008, 14 pages.
Office Action for U.S. Appl. No. 10/278,474, mailed Jan. 22, 2008, 9 pages.
Office Action for U.S. Appl. No. 10/278,474, mailed Dec. 29, 2008, 9 pages.
Office Action for U.S. Appl. No. 10/918,445, mailed Mar. 6, 2007, 11 pages.
Office Action for U.S. Appl. No. 10/918,445, mailed Jul. 24, 2008, 16 pages.
Office Action for U.S. Appl. No. 11/535,868, mailed May 23, 2008, 14 pages.
Office Action for U.S. Appl. No. 11/535,868, mailed Nov. 12, 2008, 18 pages.
Office Action for U.S. Appl. No. 11/535,868, mailed Mar. 24, 2010, 14 pages.
Office Action for Australian Appl. No. 200261843, mailed Jan. 19, 2011, 2 pages.
International Search Report for International Appl. No. PCT/US2004/003528, mailed Oct. 21, 2004, 10 pages.
Office Action for U.S. Appl. No. 10/358,252, mailed Oct. 5, 2005, 7 pages.
Office Action for U.S. Appl. No. 10/358,252, mailed Feb. 8, 2006, 6 pages.
Office Action for U.S. Appl. No. 10/918,445, mailed May 25, 2006, 42 pages.
Office Action for U.S. Appl. No. 10/918,445, mailed Oct. 12, 2006, 25 pages.
Office Action for U.S. Appl. No. 10/358,252, mailed Oct. 13, 2006, 7 pages.
Office Action for U.S. Appl. No. 10/278,474, mailed Mar. 30, 2007, 21 pages.
Office Action for U.S. Appl. No. 10/358,252, mailed Apr. 4, 2007, 6 pages.
Office Action for U.S. Appl. No. 10/358,252, mailed Jun. 4, 2007, 6 pages.
Office Action for U.S. Appl. No. 10/918,445, mailed Jun. 27, 2007, 13 pages.
Office Action for U.S. Appl. No. 10/278,474, mailed Aug. 30, 2007, 10 pages.
Office Action for U.S. Appl. No. 10/358,252, mailed Nov. 20, 2007, 7 pages.
Office Action for U.S. Appl. No. 10/918,445, mailed Dec. 28, 2007, 12 pages.
Office Action for U.S. Appl. No. 10/358,252, mailed May 14, 2008, 8 pages.
Office Action for U.S. Appl. No. 10/358,252, mailed Dec. 2, 2008, 7 pages.
Office Action for U.S. Appl. No. 10/358,242, mailed Dec. 24, 2009.
Office Action for U.S. Appl. No. 10/358,242, mailed Feb. 15, 2011.
Office Action for U.S. Appl. No. 10/358,242, mailed Oct. 18, 2011.
Office Action for U.S. Appl. No. 11/535,868, mailed Mar. 24, 2010.
Office Action for U.S. Appl. No. 12/684,722, mailed Oct. 20, 2011, 8 pages.
Office Action for U.S. Appl. No. 12/684,272, mailed Feb. 7, 2012.
Office Action for U.S. Appl. No. 12/684,752, mailed Jan. 25, 2012.
Communication Pursuant to Article 94(3) EPC for European Appl. No. 04708599.8, mailed Feb. 18, 2008.
Communication Pursuant to Article 94(3) EPC for European Appl. No. 04708599.8, mailed Apr. 30, 2009.
Communication Pursuant to Article 94(3) EPC for European Appl. No. 04708599.8, mailed Feb. 28, 2011.
Office Action in corresponding Japanese Appl. No. 2009-530498, mailed Mar. 26, 2013.
Notification of Reason for Rejection for Japanese Appl. No. 2011-039140, mailed Sep. 26, 2012.
Examiner's First Report on Australian Appl. No. 2007345245, mailed May 22, 2012.
Notice of Reasons of Rejection for Japanese Appl. No. 2008-518488, mailed Jul. 10, 2012.

\* cited by examiner

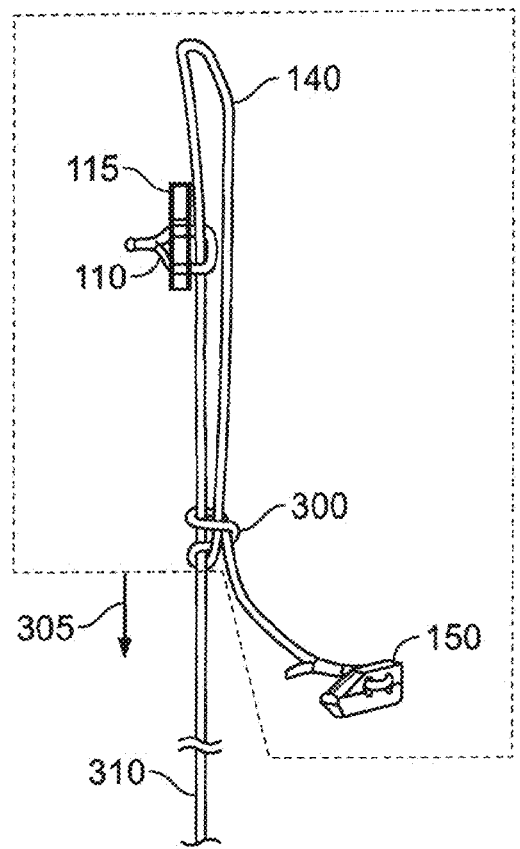

TISSUE REPAIR DEVICE

CROSS REFERENCE TO RELATED APPLICATION

This application is a continuation of, and claims priority from, U.S. Pat. No. 8,623,051, filed Aug. 2, 2011, titled "TISSUE REPAIR DEVICE," which is a divisional of U.S. patent application Ser. No. 11/165,551, filed Jun. 24, 2005, titled "TISSUE REPAIR DEVICE," now abandoned, which is incorporated herein by reference in its their entirety.

TECHNICAL FIELD

This description relates to tissue repair.

BACKGROUND

One area in the body where soft tissue is surgically reattached to bone is the attachment of a rotator cuff tendon to the humerus. The rotator cuff tendons have areas of low blood supply. With an increased blood supply, a tissue, such as a tendon, can repair and maintain itself better and faster. Thus, areas of poor blood supply in the rotator cuff make these tendons difficult and slow to heal following an injury, such as a tear to the supraspinatus muscle or the subscapularis muscle. In such a tear, part of the tendon is pulled away from the bone. Because of the poor blood supply, rather than attempting to allow an injured rotator cuff to heal on its own, a physician often recommends that the tendon be surgically repaired to better fix the position of the cuff to the bone to prevent further damage and improve the environment for healing. For example, the physician may attempt to fix the tendon to the bone using a fixation member such as a retainer or an anchor. One example of a fixation member is disclosed in U.S. Pat. No. 4,741,330 (the Hayhurst patent), which is incorporated herein by reference.

Other areas in the body also have tissue that can be surgically reattached to bone when torn from the bone or can be surgically repaired when a tear forms in the tissue. These areas include, for example, the biceps tendon, the lateral collateral ligament in the knee, the medial collateral ligament in the knee, the meniscus in the knee, the popliteal ligament in the leg, and the labrum tendon in the knee.

Fibrous tissue wounds, such as muscle, ligament, and cartilage tears, can be repaired arthroscopically using flexible members such as sutures. Traditionally, to close a fibrous tissue wound, a surgeon would insert two suture needles into the tissue with sutures attached, thread the sutures across the wound, and then tie knots to fix the free ends of the sutures within the tissue.

To simplify the wound closure procedure and to improve fixation, various types of fixation members have been developed. One example of a fixation member in the form of a retainer is disclosed in the Hayhurst patent. In the Hayhurst patent, one end of a flexible member is fixed to a resiliently-deformable, bar-shaped retainer. The retainer is loaded into the bore of a hollow needle and deployed into or against the fibrous tissue. The surgeon then threads the flexible member across the wound and tensions a free end of the suture to pull the wound closed. When the surgeon tensions the suture, the bar in the retainer becomes oriented transversely to the suture hole, holding the suture in place.

SUMMARY

In one general aspect, a tissue repair device includes a closed loop of multifilament flexible material. The loop is knotless and includes a contact portion in which ends of the multifilament flexible material are interwoven and melted-formed.

Implementations can include one or more of the following features. For example, the tissue repair device can include a fixation member having a structure that defines a cavity that receives at least a part of the closed loop.

The tissue repair device can include a flexible member traversing the loop. The flexible member can traverse the loop by being passed through an interior defined by the loop. The flexible member can traverse the loop by being passed through the multifilament flexible material.

The ends of the multifilament flexible material can be thermally fused together within the contact portion. The flexible member can traverse the loop by being passed through the thermally fused portion of the multifilament flexible material.

The multifilament flexible material can be made of polymer-based compound.

The flexible member can traverse the loop by being passed through the interwoven portion of the multifilament flexible material. The multifilament flexible material can be braided or twisted.

In another general aspect, a tissue repair device is made by forming a closed loop from the multifilament flexible material. The forming includes interweaving ends of the multifilament flexible material together to form a contact portion without tying the ends together in a knot, and causing the ends of the multifilament flexible material to melt in the contact portion.

Implementations can include one or more of the following features. For example, the method can also include passing at least a part of the multifilament flexible material through a cavity defined by a fixation member.

The method can include traversing a flexible member through the loop. The traversing can include passing the flexible member through an interior defined by the loop. The traversing can include passing the flexible member through the multifilament flexible material. The traversing can include passing the flexible member through the contact portion of the multifilament flexible material.

Forming the closed loop can include thermally fusing the ends of the multifilament flexible material in the contact portion. Forming the closed loop from the multifilament flexible material can include forming without applying a filler material to the ends of the flexible element.

In another general aspect, a tissue repair device includes a closed loop of multifilament flexible material, and a fixation member. The loop is knotless and includes a contact portion in which ends of the multifilament flexible material are interwoven. The fixation member has a structure that defines a cavity that receives at least a part of the closed loop.

In another general aspect, a tissue repair device includes a fixation member having a structure that defines a cavity, a multifilament flexible element, and a flexible member. The multifilament flexible element includes a part that is within the cavity, and a thermally fused end. The flexible member passes at least partially through the thermally fused end of the multifilament flexible element.

Implementations can include one or more of the following features. In particular, the multifilament flexible element includes another thermally fused end and the flexible member passes through the other thermally fused end of the multifilament flexible element.

Aspects of the device and method may include one or more of the following advantages. The ends of the multifilament flexible material are thermally fused together without the use of a filler material. The loop acts as a pulley that reduces pinching of the flexible member between the tissue and the fixation member during deployment. Additionally, the pulley design enables the flexible member to slide relative to the fixation member without being impeded by the edges of the fixation member or by the tissue when the fixation member is deployed in tissue.

Other features will be apparent from the description, the drawings, and the claims.

DESCRIPTION OF DRAWINGS

FIGS. 3A-3C are side perspective views showing formation of a retaining element that can be formed in the tissue repair device of FIG. 1A.

FIG. 4 is a flow chart of a procedure for forming the loop in the tissue repair device of FIG. 1A.

Like reference symbols in the various drawings may indicate like elements.

DETAILED DESCRIPTION

Figure 1A:
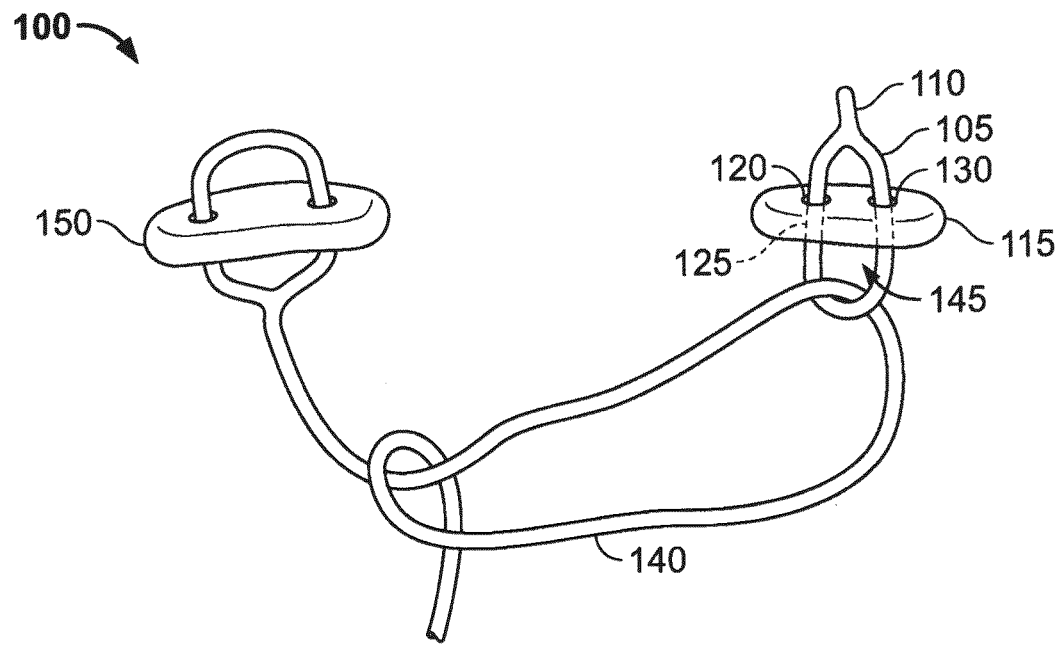
FIG. 1A is a perspective view of a tissue repair device.

Referring to FIGS. 1A-1C and 2, a tissue repair device 100 includes a closed loop 105 of multifilament flexible material. The loop 105 is knotless, that is, the loop 105 is formed without tying ends of the multifilament flexible material together into a knot. The multifilament flexible material is a material suitable for implantation into hard or soft human tissue and it may be absorbable or nonabsorbable. The multifilament flexible material has two or more fibers or strands that are twisted, braided, or otherwise interlinked about each other. The multifilament flexible material is capable of being flexed or bent. The loop 105 is closed, with a first end of the multifilament flexible material contacts a second end of the multifilament flexible material to form a contact portion 110.

The tissue repair device 100 also includes a fixation member 115 defining a cavity 120 that receives a part 125 of the loop 105. As shown, the fixation member 115 can also include a second cavity 130 that receives another part 135 of the loop 105. The fixation member 115 can be made of any rigid material suitable for implantation into hard or soft human tissue. For example, the fixation member 115 can be made of a biocompatible plastic, a biocompatible metal, or a bioabsorbable polymer.

Figure 1B:
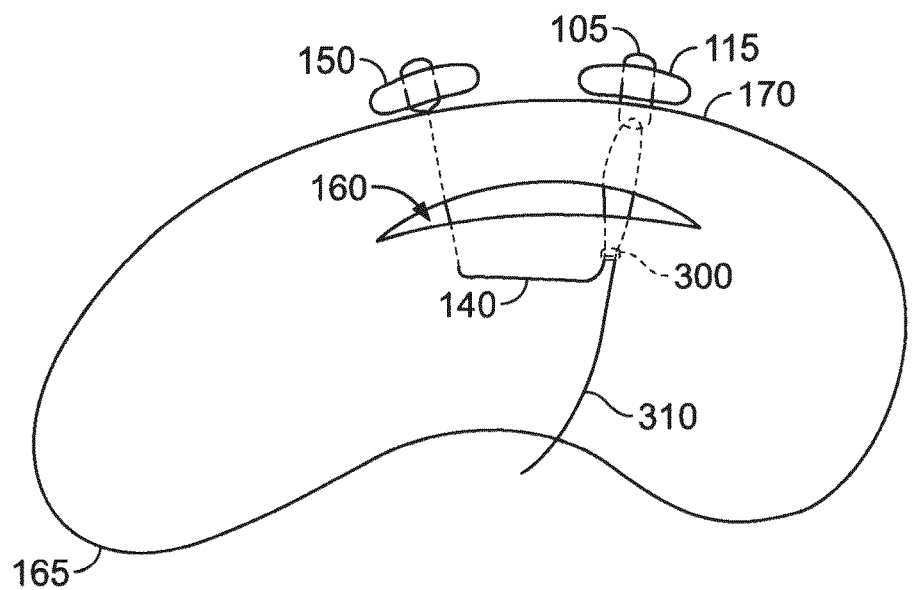
FIG. 1B is an illustration of the tissue repair device of FIG. 1A, shown mending a tear in soft tissue.
Figure 1C:
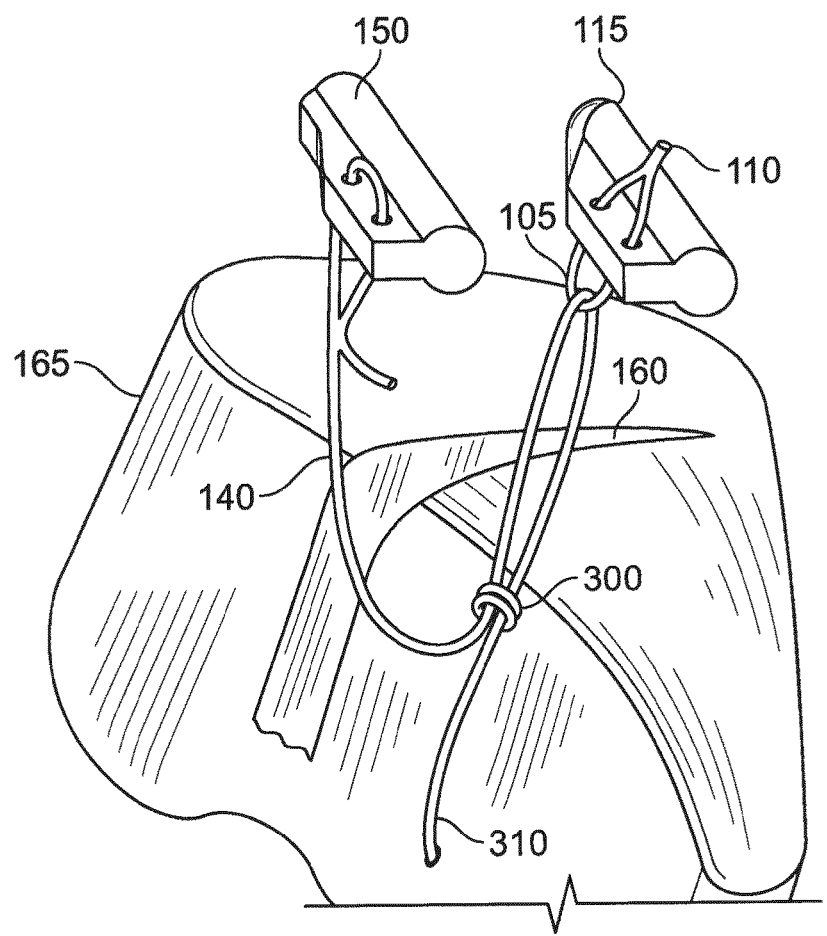
FIG. 1C is a perspective view of the tissue repair device of FIG. 1A, shown mending a tear in soft tissue.
Figure 2:
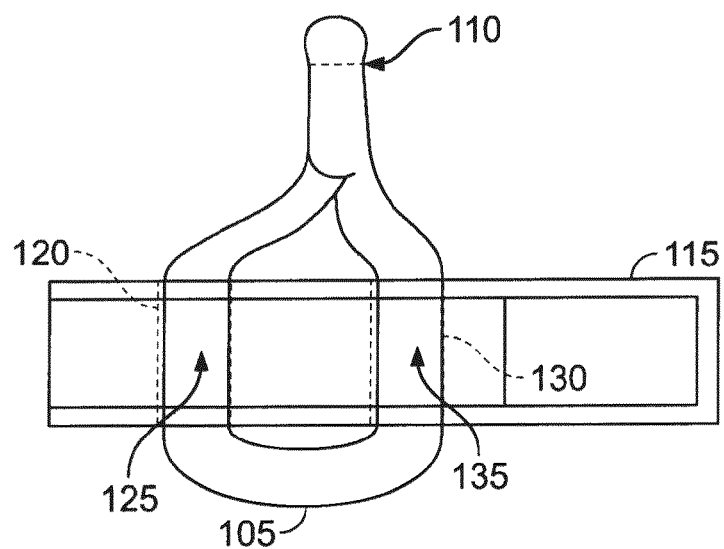
FIG. 2 is a side cross-sectional view of a fixation member and a loop of the tissue repair device of FIG. 1A.

The fixation member 115 can be formed as a retainer that is transferred through a tear 160 in tissue 165 and held at an outer surface 170 of the tissue 165 after deployment, as shown in FIGS. 1B and 1C.

The fixation member 115 can be formed as an anchor or a screw that is drilled or driven into the tissue during deployment, as shown in FIG. 15 of U.S. application Ser. No. 09/704,926. In an anchor or screw form, the fixation member 115 can include one or more threads on its outer surface to facilitate holding of the fixation member 115 to the tissue. Such anchor or screw forms are particularly adapted for use in hard tissue such as bone. The fixation member 115 can be formed with a generally cylindrical shape for receipt within a delivery device, such as a needle. The fixation member 115 can have a fin extending from its generally cylindrical shape.

The tissue repair device 100 also includes a flexible member 140, for example, a suture, that traverses the loop 105. As shown in FIGS. 1A and 1B, the flexible member 140 traverses the loop 105 by being passed through an interior 145 of the loop 105 that is bounded by or enclosed by the loop 105 and the fixation member 115. The flexible member 140 is a material suitable for implantation into hard or soft human tissue and it may be absorbable or nonabsorbable in the tissue after implantation. For example, the flexible member 140 can be made of a natural material, such as, for example, collagen, surgical silk, surgical cotton, or surgical steel. As another example, the flexible member 140 can be made of a synthetic material, such as, for example, a polymer or nylon.

Figure 3A:
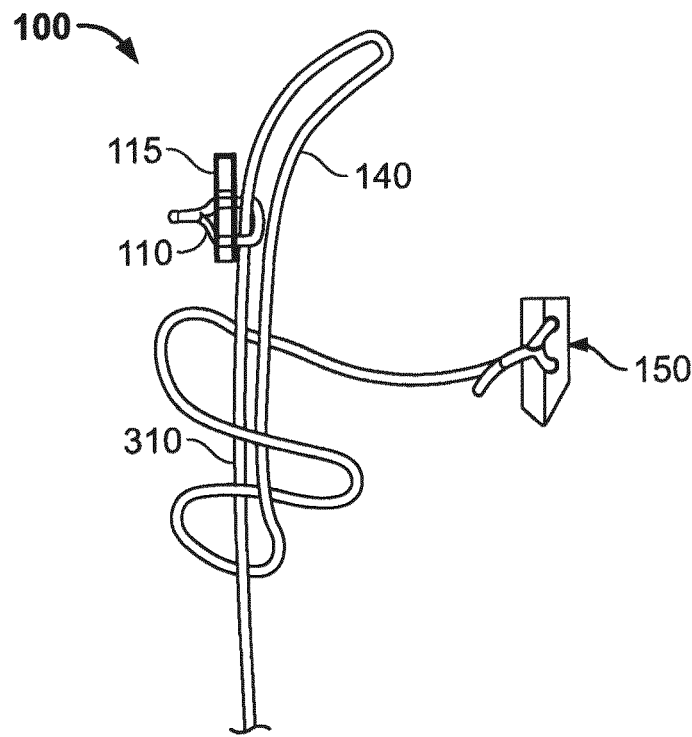
Figure 3B:
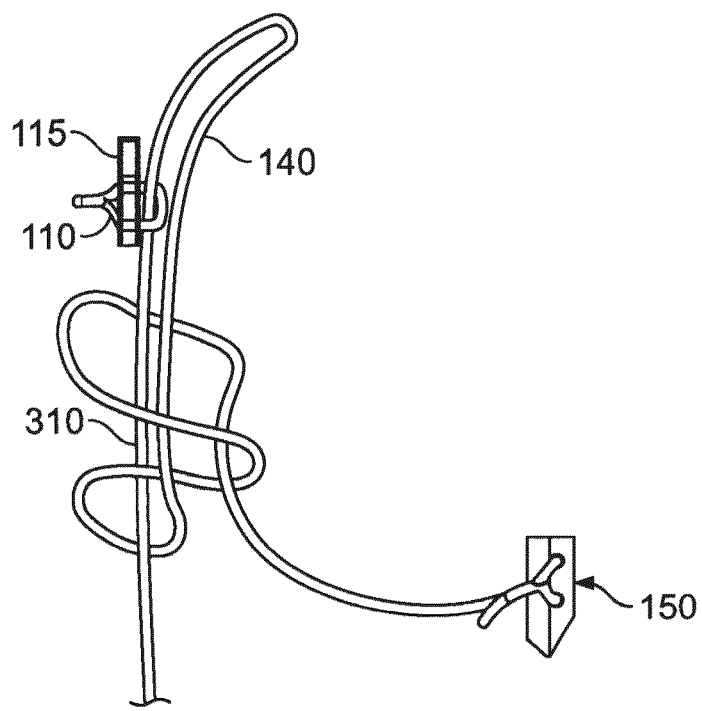

Referring also to FIGS. 3A-3C, the tissue repair device 100 can include a second fixation member 150 through which the flexible member 140 is passed, and a retaining element 300, for example, a slip knot in the flexible member 140. The flexible member 140 is passed through the fixation member 150 by threading the flexible member 140 through a hole within the fixation member 150 and then attaching an end of the flexible member 140 to a region of the flexible member 140 that has not been threaded through the fixation member 150. The retaining element 300 permits the flexible member 140 to be pulled in the direction of arrow 305 and pass through the retaining element 300, thus reducing the distance between the fixation member 115 and the fixation member 150 and causing sides of the tear 160 to come into contact with each other. The retaining element 300 prevents an increase in distance between the fixation member 115 and the fixation member 150 to prevent the sides of the tear 160 from coming apart after coming in contact with each other.

Examples of the fixation members 115, 150, the retaining element 300, and the flexible member 140 can be found in U.S. application Ser. No. 10/918,445, filed Aug. 16, 2004, which is incorporated herein by reference.

Figure 5A:
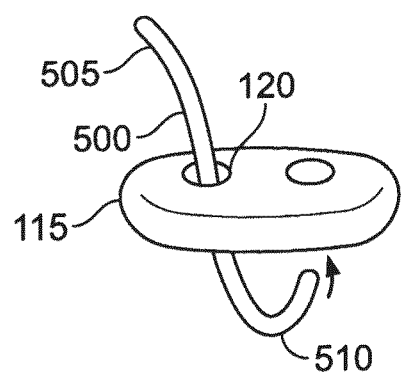
FIGS. 5A-5E show perspective views of the multifilament flexible material that is formed into the loop in the procedure of FIG. 4.
Figure 5B:
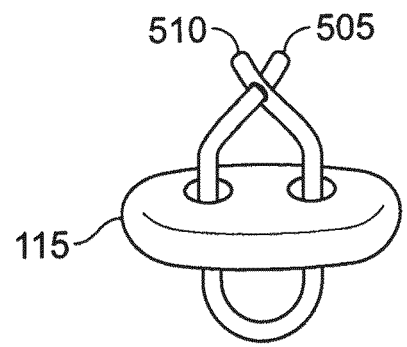
Figure 5C:
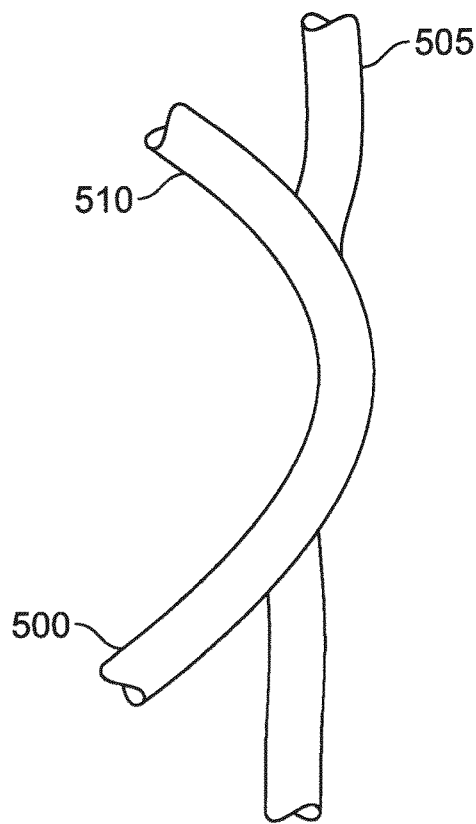
Figure 5D:
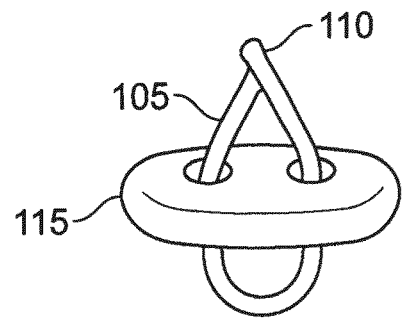
Figure 5E:
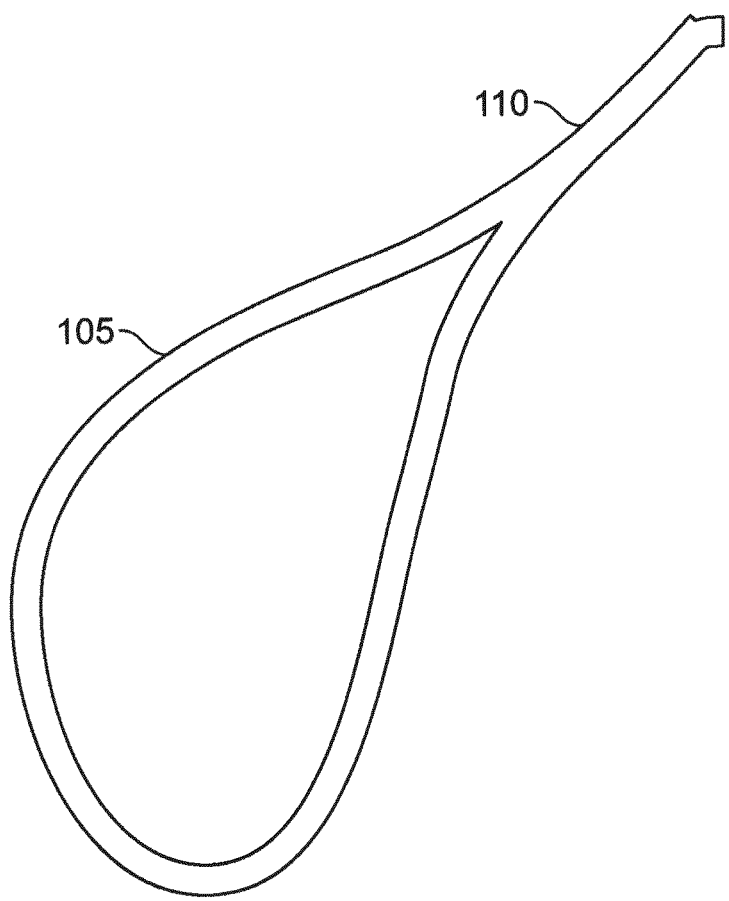

Referring to FIGS. 4 and 5A-5E, a procedure 400 is performed to form the loop 105. Initially, a first end 510 of the multifilament flexible material 500 is inserted or passed through the cavity 120 of the fixation member 115 (step 405). If desired, the multifilament flexible material 500 can be inserted through the second cavity 130 of the fixation member fixation member 115. After insertion, the first end 510 of the material 500 is brought into contact with a second end 505 (step 410). To facilitate thermal fusion, the ends 505, 510 can be interwoven into each other to make contact, as shown in FIG. 5B. In this case, the fibers of the end 505 are interwoven with the fibers of the end 510. For example, the end 505 can be inserted between fibers of the end 510, as shown in FIG. 5B. As another example, the end 505 can be inserted through an interior of a Chinese trap formed at the end 510, as shown in FIG. 5C.

Next, energy is supplied to the ends 505, 510 until the temperature of the ends 505, 510 raises to the point that the material in the ends 505, 510 melts or liquefies (step 415). At this point, the ends 505, 510 blend together to form a blended region, that is, a uniform or homogenous composition. Energy is supplied to the ends 505, 510 using, for example, thermal energy, ultrasonic energy, laser light, or electrical arc discharge. The ends 505, 510 can be inserted in a suitable energy supplying apparatus, depending on the way in which energy is provided to the ends 505, 510. For example, if the energy supplied is thermal energy, the ends 505, 510 can be locally heated using a heater element such as an electrical resistance heater element in the form of a thin film of an alloy. The heater element can create heat by other means, such as by induction, irradiation, or a chemical reaction. The blended region is allowed to cool to form a solid blended composition in the contact portion 110 (step 420).

The multifilament flexible material can be any material that is able to melt or liquefy upon application of an energy that raises its temperature and to solidify upon cooling such that the multifilament flexible material forms a blended region. Examples of materials having these properties include nylon, metals (such as titanium or steel), and polymer-based compounds, such as polyester fiber, polypropylene, polybutester, polyglactin, poliglecaprone, and polydioxanone. Another material that may have these properties is natural silk protein produced by spiders. The multifilament flexible material 500 can be any length and diameter that enables passage through the fixation member 615 and subsequent thermal fusion. For example, in one implementation in which the flexible material 500 is a type 0 size, the material 500 is about 4-12 mm long and has a diameter of about 0.4 mm.

The procedure 400 produces a contact portion 110 that has a yielding strength that is equivalent to or near to the United States Pharmacopoeia (USP) Standards value for a particular size of suture. For example, for a USP type 0 size suture, the yielding strength of the contact portion is about 12-13 pounds.

Figure 6:
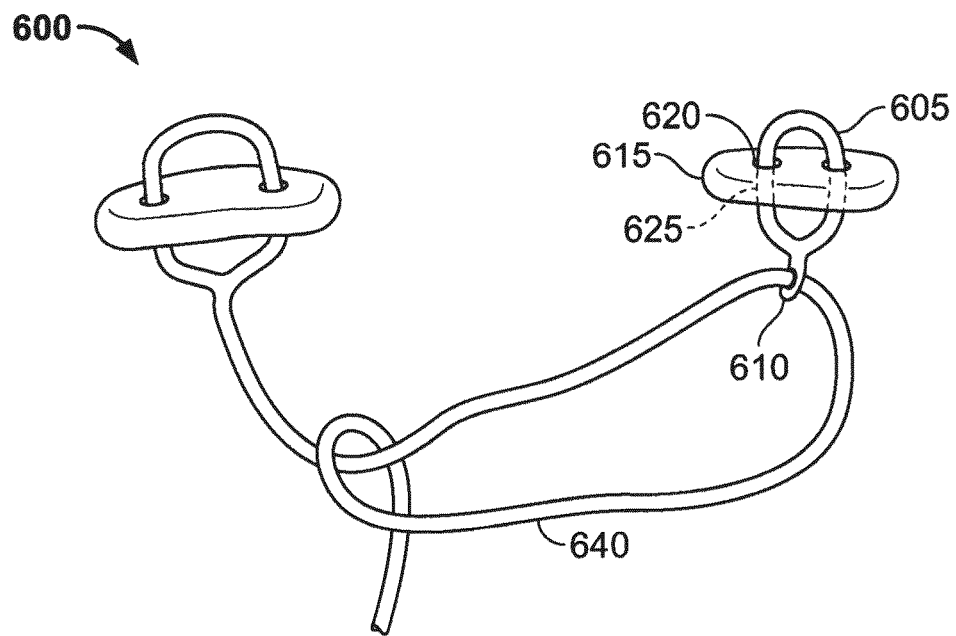
FIG. 6 is a perspective view of another implementation of a tissue repair device.

Referring to FIG. 6, in another implementation, a tissue repair device 600 includes a closed loop 605 of multifilament flexible material, similar in design to the loop 105 described above. The loop 605 is closed, thus, a first end of the multifilament flexible material contacts a second end of the multifilament flexible material to form a contact portion 610. One or more of the ends of the multifilament flexible material may include a Chinese trap.

The tissue repair device 600 also includes a fixation member 615 defining a cavity 620 that receives a part 625 of the loop 605, as discussed above with respect to FIG. 2. The tissue repair device 600 also includes a flexible member 640 that traverses the loop 605. As shown, the flexible member 640, in this implementation, traverses the loop 605 by passing through the contact portion 610 of the multifilament flexible material rather than passing through the interior of the loop 605. In this way, the flexible member 640 freely moves through the contact portion 610. For example, if the contact portion 610 includes a Chinese trap, then the flexible member 640 would pass directly through the Chinese trap.

Referring again to FIGS. 1B and 1C, the loop 105, 605 acts like a pulley through which the flexible member 140, 640 can freely slide to facilitate deployment of the fixation member 115, 615 into tissue 165. The pulley design reduces pinching of the flexible member 140, 640 between the surface 170 of the tissue 165 and the fixation member 115, 615 during deployment. Additionally, the loop 105 reduces friction between the flexible member 140, 640 and the fixation member 115, 615, thus enabling the flexible member 140, 640 to slide without being impeded by the edges of the fixation member 115, 615 or by the tissue 165 when the fixation member 115, 615 is deployed in tissue 165. Other pulley designs are shown in U.S. application Ser. No. 09/704,926. The device 100 or 600 can be delivered to the tissue 165 using a delivery device, such as, for example, the delivery devices shown in FIGS. 3, 5, 6, and 8-11 of U.S. application Ser. No. 09/704,926.

Figure 7:
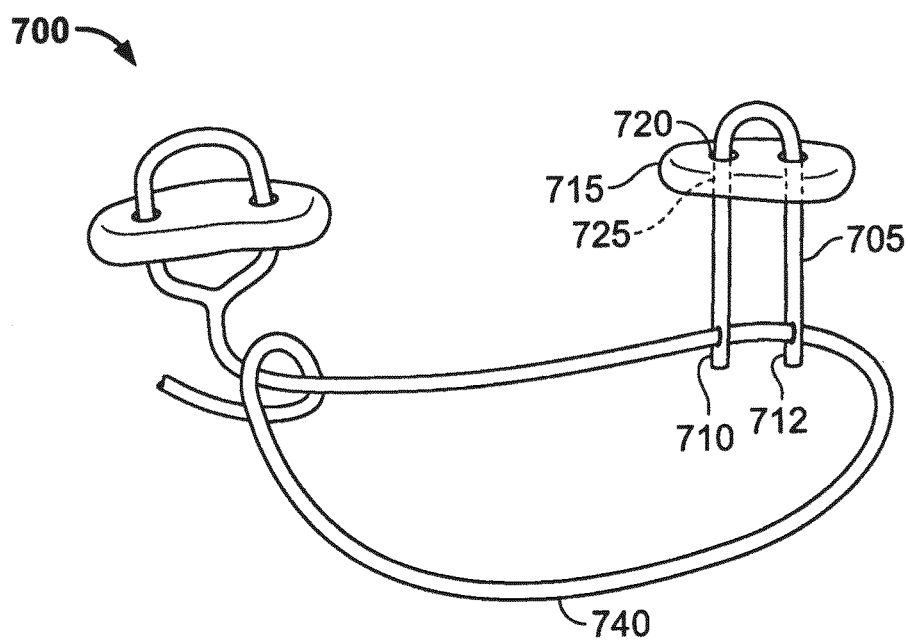
FIG. 7 is a perspective view of another implementation of a tissue repair device.

Referring to FIG. 7, in another implementation, a tissue repair device 700 includes a multifilament flexible element 705 having a thermally fused end 710 and a part 725 that is within a cavity 720 defined by a fixation member 715. Unlike the ends 505, 510 of the multifilament flexible material of the loop 105, the end 710 is thermally fused without being contacted to a second end 712 of the element 705. In this implementation, energy is supplied to the end 710 until the temperature of the end 710 raises to the point that the material in the end 710 melts or liquefies and blends together to form a blended, uniform composition. Energy may be supplied in any one of the manners mentioned above. Next, the blended composition at the end 710 is allowed to cool to form a solid blended composition.

The multifilament flexible element 705 can be any length and diameter that facilitates passage through the fixation member 715 and subsequent thermal fusion of the end 710. For example, in one implementation in which the flexible material 705 is a type 0 size, the material 500 is about 4-12 mm long and has a diameter of about 0.4 mm.

The tissue repair device 700 includes a flexible member 740 that is passed at least partially through the thermally fused end 710 by, for example, threading the flexible member 740 through the end 710 using a needle. After the flexible member 740 is passed through the end 710, it is free to move relative to the end 710. Thus, the multifilament flexible element 705 acts like a pulley through which the flexible member 740 can freely slide to facilitate deployment of the fixation member 715 into tissue.

To improve pullout strength between the flexible member 740 and the flexible element 705, the second end 712 of the element 705 can also be thermally fused (as discussed above with respect to the end 710) and the flexible member 740 can be passed through the thermally fused end 712, as shown.

Other implementations are within the scope of the following claims.

For example, the multifilament flexible material or the contact portion may include a growth factor, such as, for example, an angiogenic factor. The multifilament flexible material or the contact portion may be loaded with a bioactive material, a stimulant, or any substance that promotes healing of the tissue.

As another example, the contact portion can be formed by stitching the ends of the multifilament flexible material together without raising the temperature at the ends by using an additional element of similar ligature as the thread. For example, if the multifilament flexible material is a type 0 size, then the thread can be a high strength polyethylene suture of 2-0, 4-0, or 8-0 size using the USP standards.

What is claimed is:

1. A tissue repair device comprising:
   a closed loop of multifilament flexible material, wherein the loop is knotless and includes a contact portion in which ends of the multifilament flexible material are interwoven and form a blended region having a uniform or homogenous composition when energy sufficient to melt or liquefy the ends is supplied to the ends of the multifilament flexible material;
   a substantially rigid first fixation member having a structure that defines first and second through holes, the first through hole receiving a first part of the closed loop of multifilament flexible material and the second through hole receiving a second part of the closed loop of multifilament flexible material; and
   a flexible member slidably received through the contact portion of the closed loop and having an end that passes through an opening defined in a second fixation member and passes through a region of the flexible member that has not been passed through the second fixation member to form a second, knotless closed loop to secure the second fixation member to the flexible member.

2. The tissue repair device of claim 1 wherein the contact portion comprises a Chinese trap.

3. A tissue repair device comprising:
 a closed loop of multifilament flexible material, wherein the loop is knotless and includes a contact portion in which ends of the multifilament flexible material are interwoven and form a blended region having a uniform or homogenous composition when energy sufficient to melt or liquefy the ends is supplied to the ends of the multifilament flexible material;
 first and second substantially rigid fixation members, the first fixation member having a structure defining first and second through holes, the first through hole receiving a first part of the closed loop of multifilament flexible material and the second through hole receiving a second part of the closed loop of multifilament flexible material, and the second fixation member having a structure defining an opening; and
 a flexible member slidably received through the contact portion of the closed loop and having an end that passes through the opening in the second fixation member and passes through a region of the flexible member that has not been passed through the second fixation member to form a second, knotless closed loop to secure the second fixation member to the flexible member.

4. The tissue repair device of claim 3 wherein the contact portion comprises a Chinese trap.

\* \* \* \* \*